[54] O-PYRAZOLOPYRIMIDINE-(THIONO)-PHOSPHORIC(PHOSPHONIC) ACID ESTERS

[75] Inventors: Hellmut Hoffmann, Wuppertal; Ingeborg Hammann, Cologne, both of Germany

[73] Assignee: Bayer Aktiengesellschaft, Leverkusen, Germany

[22] Filed: Aug. 8, 1973

[21] Appl. No.: 386,684

[30] Foreign Application Priority Data
Aug. 23, 1972 Germany............................ 2241395

[52] U.S. Cl. 260/256.4 E; 260/256.4 R; 260/256.4 F; 424/200
[51] Int. Cl.² ........................................ C07D 239/00
[58] Field of Search ............... 260/256.4 E, 256.5 R

[56] References Cited
UNITED STATES PATENTS

| | | | |
|---|---|---|---|
| 3,402,176 | 9/1968 | Schicke........................ | 260/256.4 E |
| 3,478,029 | 11/1969 | Schicke........................ | 260/256.4 E |
| 3,496,178 | 2/1970 | Scherer et al. ............... | 260/256.4 E |
| 3,761,479 | 9/1973 | Hoffman et al. .............. | 260/256.4 E |

Primary Examiner—Richard J. Gallagher
Assistant Examiner—James H. Turnipseed
Attorney, Agent, or Firm—Burgess, Dinklage & Sprung

[57] ABSTRACT

O-pyrazolopyrimidine-(thiono)-phosphoric (phosphonic) acid esters of the formula

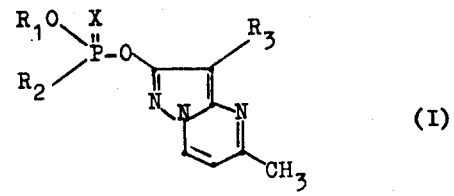

(I)

in which
  $R_1$ is alkyl of 1 to 6 carbon atoms,
  $R_2$ is alkyl of 1 to 4 carbon atoms, alkoxy of 1 to 6 carbon atoms or phenyl,
  $R_3$ is hydrogen, chlorine or bromine, and
  X denotes oxygen or sulfur, which possess insecticidal and acaricidal properties.

7 Claims, No Drawings

O-PYRAZOLOPYRIMIDINE-(THIONO)-PHOSPHORIC(PHOSPHONIC) ACID ESTERS

The present invention relates to and has for its objects the provision of particular new O-pyrazolopyrimidine-(thiono)-phosphoric (phosphonic) acid esters which are optionally halogen-substituted on the pyrazole ring, which possess insecticidal and acaricidal properties, active compositions in the form of mixtures of such compounds with solid and liquid dispersible carrier vehicles, and methods for producing such compounds and for using such compounds in a new way especially for combating pests, e.g., insects and acarids, with other and further objects becoming apparent from a study of the within specification and accompanying examples.

It is known from Belgian Patent Specification 676,802 and published Netherlands Patent Application No. 6,516,907 that O-pyrazolopyrimidine-(thiono)-phosphoric(phosphonic, phosphinic) acid ester derivatives, for example O,O-diethyl-O-[5,7-dimethyl-pyrazolo(1,5-α)-pyrimidin-(2)yl]-thiono-phosphoric acid ester (Compound A) and O-ethyl-ethane-O-[5,7-dimethylpyrazolo-(1,5-α)-pyrimidin-(2)yl]-thiono-phosphonic acid ester (Compound B) possess a pesticidal, especially insecticidal and acaricidal, action.

The present invention provides O-pyrazolopyrimidine-(thiono)-phosphoric(phosphonic) acid esters of the general formula

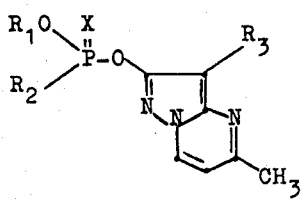

(I)

in which
R₁ is alkyl of 1 to 6 carbon atoms,
R₂ is alkyl of 1 to 4 carbon atoms, alkoxy of 1 to 6 carbon atoms or phenyl,
R₃ is hydrogen, chlorine or bromine, and
X denotes oxygen or sulfur.

Preferably, R₁ is straight-chain or branched lower alkyl of 1 to 4 carbon atoms, and R₂ is lower alkyl of 1 to 3 carbon atoms, lower alkoxy of 1 to 4 carbon atoms or phenyl.

Surprisingly, the O-pyrazolopyrimidine-(thiono)-phosphoric(phosphonic) acid esters according to the invention, of the formula (I), have a considerably higher insecticidal, especially soil-insecticidal, and acaricidal action than previously known compounds of analogous structure and of the same type of action. The compounds according to the invention thus represent a genuine enrichment of the art.

Furthermore, the compounds according to the invention contribute towards meeting the great need for constantly new active compounds in the field of pesticides. The latter arises from the fact that the commercially available agents are required to meet constantly higher standards, particularly with regard to the protection of the environment, such as low toxicity to warm-blooded animals and low phytotoxicity, rapid degradation in and on the plant with short minimum intervals to be observed between spraying with pesticide and harvesting, and effectiveness against resistant pests.

The present invention also provides a process for the production of an O-pyrazolopyrimidine-(thiono)-phosphoric (phosphonic) acid ester derivative of the formula (I) in which a (thiono)phosphoric(phosphonic) acid ester halide of the general formula.

(II)

is reacted with a 2-hydroxypyrazolopyriidine derivative of the general formula

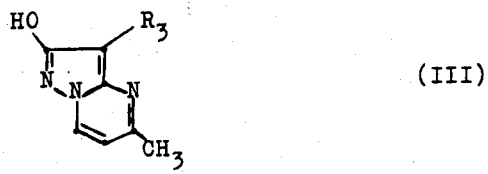

(III)

in which
R₁, R₂, R₃ and X have the abovementioned meanings and
Hal denotes halogen, preferably chlorine, in the presence of an acid acceptor or in the form of an alkali metal, alkaline earth metal or ammonium salt.

If O-ethyl-ethanephosphonic acid ester chloride and 2-hydroxy-5-methyl-pyrazolo(1,5-α)-pyrimidine are used as starting substances, the course of the reaction can be represented by the following formula scheme:

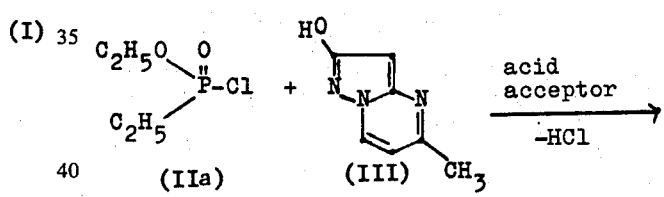

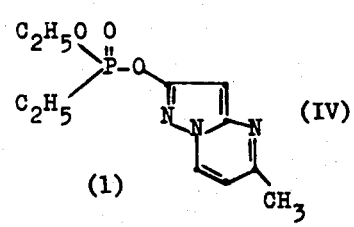

(1)

The following are specific examples of (thiono)phosphoric(phosphonic) acid ester halides (II) which can be used: O,O-dimetyl-, O,O-diethyl, O,O-dipropyl-, O,O-di-iso-propyl,- O,O-dibutyl-, O,O-di-tert.-butyl-, O-methyl-O-ethyl, O-methyl-O-iso-propyl-, O-methyl-O-butyl-, O-ethyl-O-iso-propyl- and O-ethyl-O-butyl-phosphoric acid ester chloride or bromide and their thiono analogues, and also O-methyl-methane-, O-methyl-ethane-, O-ethyl-methane-, O-propyl-methane-, O-propyl-ethane-, O-iso-propyl-methane-, O-iso-propyl-ethane-, O-butyl-methane-, O-butyl-ethane-, O-tert.-butyl-methane-, O-ethyl-iso-propane-, O-methyl-phenyl, O-ethyl-phenyl- and O-propyl-phenyl-phosphonic acid ester chloride or bromide and the corresponding thiono analogues.

The (thiono)phosphoric(phosphonic) acid ester halides (II) are known and can be prepared by customary processes.

The 2-hydroxy-pyrazolopyrimidines (III) may be obtained from 3-hydroxy-5-amino-pyrazole and sodium formylacetone, optionally with subsequent halogenation in the 3-position.

The process according to the invention is preferably carried out with the use of a solvent or diluent. Practically all inert organic solvents can be used for this purpose. Preferred examples include aliphatic and aromatic (optionally chlorinated) hydrocarbons, such as benzene, toluene, xylene, benzine, methylene chloride, chloroform, carbon tetrachloride and chlorobenzene, ethers, for example diethyl ether, dibutyl ether and dioxane, ketones, for example acetone, methyl ethyl ketone, methyl isopropyl ketone and methyl isobutyl ketone, and especially nitriles, such as acetonitrile and propionitrile.

All customary acid-binding agents can be used as acid acceptors. Those which have been found particularly valuable are alkali metal carbonates and alkali metal alcoholates, such as sodium carbonate and potassium carbonate, sodium methylate and ethylate and potassium methylate and ethylate, and also aliphatic, aromatic or heterocyclic amines, for example triethylamine, dimethylamine, dimethylaniline, dimethylbenzylamine and pyridine.

The reaction temperature can be varied within a wide range. In general, the reaction is carried out at 0 to 100, preferably at 25 to 65°C.

In general, the reaction is carried out under normal pressure.

In carrying out the process, the starting compounds are generally employed in equimolar ratios. An excess of one or other reactant seems to produce no significant advantages. The reaction is preferably carried out in the presence of one of the abovementioned solvents and in the presence of an acid acceptor, at the indicated temperatures, and the reaction mixture may be worked up in the usual manner after stirring for several hours.

The compounds according to the invention are obtained in a crystalline form. They are characterized by the melting point.

As has already been mentioned, the new O-pyrazolopyrimidine-(thiono)-phosphoric(phosphonic) acid esters are distinguished by an excellent insecticidal, especially soil-insecticidal, and acaricidal activity against plant pests, hygiene pests and pests of stored products. They possess a good action both against sucking and against biting insects and mites (Acarina). At the same time, their phytotoxicity is low.

For these reasons, the products according to the invention are successfully employed as pesticides in plant protection and the protection of stored products, and in the hygiene field.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (Cimex lectularius), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the bloosom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or Sitophilus zeamais), the drugstore beetle (Stegobium paniceum), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (Blatta orientalis), the giant cockroach (*Blaberus giganteus*) and the black giant cockroach (*Blaberus fuscus*) as well as Henschoutedenia flexivitta; further, Orthoptera, for example the house cricket (*Acheta domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and blue bottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl celulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm³ of the preparation of the active compound was applied with a pipette to a filter paper disc of 7 cm diameter. The wet disc was placed in a glass vessel containing 50 vinegar flies (*Drosophila melanogaster*) and covered with a glass plate.

After the specified periods of time, the destruction was determined as a percentage: 100% means that all the flies were killed; 0% means that none of the flies were killed.

The active compounds, their concentrations, the evaluation times and the degree of destruction can be seen from the following Table 1:

Table 1

| (*Drosophila* test) Active compound | Active compound concentration in % by weight | Degree of destruction in % after 1 day |
|---|---|---|

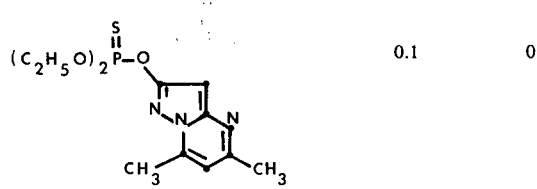

(Known)   A

| | 0.1 | 0 |

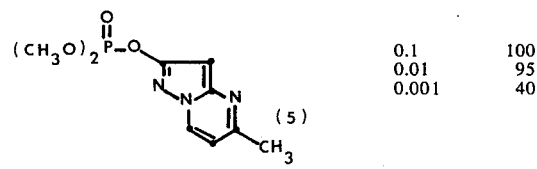

(5)

| | 0.1 | 100 |
| | 0.01 | 95 |
| | 0.001 | 40 |

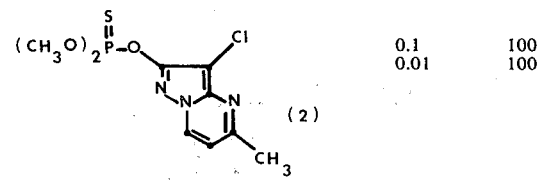

(2)

| | 0.1 | 100 |
| | 0.01 | 100 |

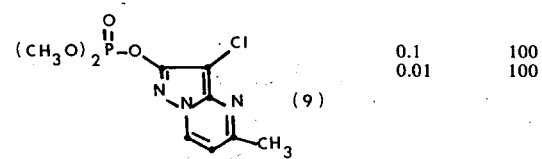

(9)

| | 0.1 | 100 |
| | 0.01 | 100 |

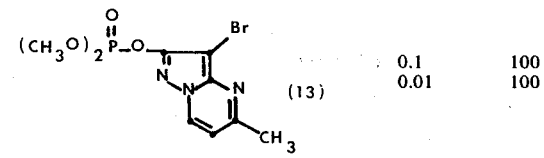

(13)

| | 0.1 | 100 |
| | 0.01 | 100 |

Table 1-continued
| Active compound (*Drosophila* test) | Active compound concentration in % by weight | Degree of destruction in % after 1 day |
|---|---|---|
| 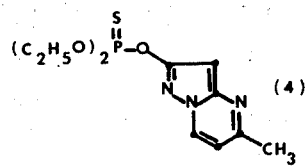 (4) | 0.1<br>0.01 | 100<br>100 |
| 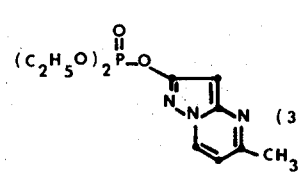 (3) | 0.1<br>0.01 | 100<br>90 |
| 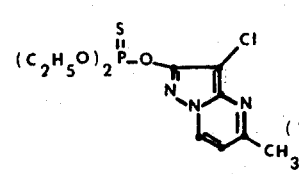 (10) | 0.1<br>0.01 | 100<br>100 |
| 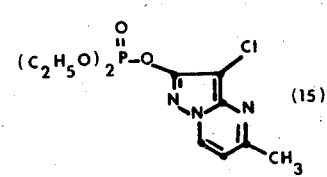 (15) | 0.1<br>0.01 | 100<br>100 |
| 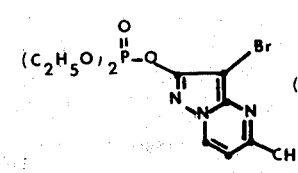 (12) | 0.1<br>0.01 | 100<br>98 |
| 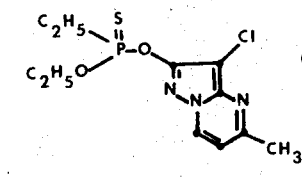 (16) | 0.1<br>0.01 | 100<br>100 |
EXAMPLE 2
Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 2:

Table 2
(*Plutella* test)

| Active compound | Active compound concentration in % by weight | Degree of destruction in % after 3 days |
| --- | --- | --- |
| (known) (A) | 0.1 <br> 0.01 <br> 0.001 | 100 <br> 100 <br> 0 |
| (known) (B) | 0.1 <br> 0.01 <br> 0.001 | 100 <br> 100 <br> 0 |
| (5) | 0.1 <br> 0.01 <br> 0.001 | 100 <br> 100 <br> 100 |
| (2) | 0.1 <br> 0.01 <br> 0.001 | 100 <br> 100 <br> 100 |
| (9) | 0.1 <br> 0.01 <br> 0.001 | 100 <br> 100 <br> 85 |

Table 2-continued

| (Plutella test) Active compound | Active compound concentration in % by weight | Degree of destruction in % after 3 days |
| --- | --- | --- |
| 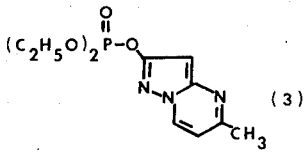 (3) | 0.1<br>0.01<br>0.001 | 100<br>100<br>100 |
| 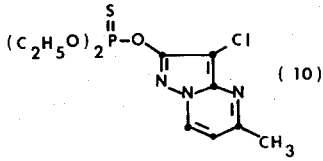 (10) | 0.1<br>0.01<br>0.001 | 100<br>100<br>95 |
| 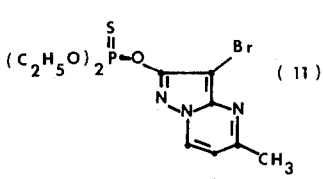 (11) | 0.1<br>0.01<br>0.001 | 100<br>100<br>100 |
| 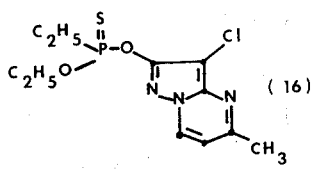 (16) | 0.1<br>0.01<br>0.001 | 100<br>100<br>100 |

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 3:

Table 3
| Active compound (*Myzus* test) | | Active compound concentration in % by weight | Degree of destruction in % after 1 day |
|---|---|---|---|
| 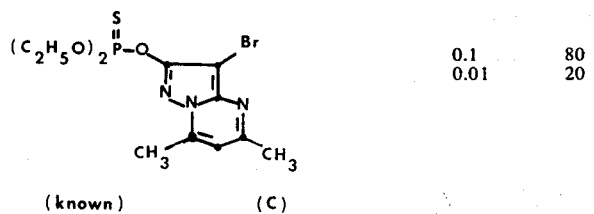 (known) (C) | | 0.1<br>0.01 | 80<br>20 |
| 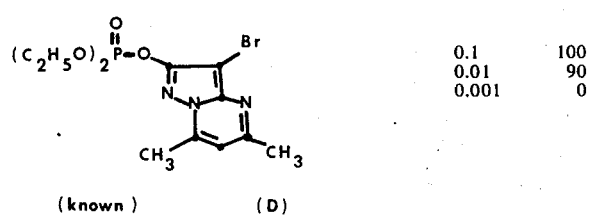 (known) (D) | | 0.1<br>0.01<br>0.001 | 100<br>90<br>0 |
| 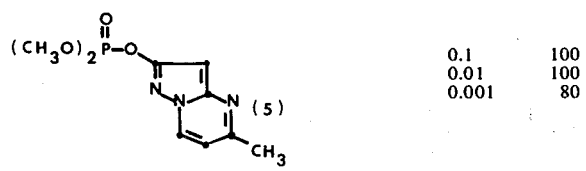 (5) | | 0.1<br>0.01<br>0.001 | 100<br>100<br>80 |
| 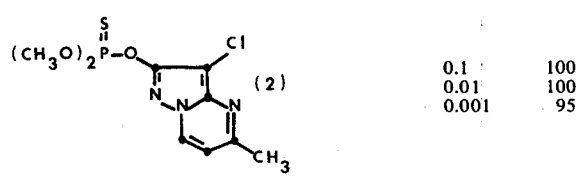 (2) | | 0.1<br>0.01<br>0.001 | 100<br>100<br>95 |
| 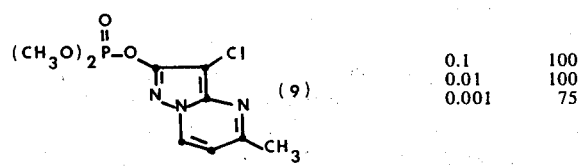 (9) | | 0.1<br>0.01<br>0.001 | 100<br>100<br>75 |
| 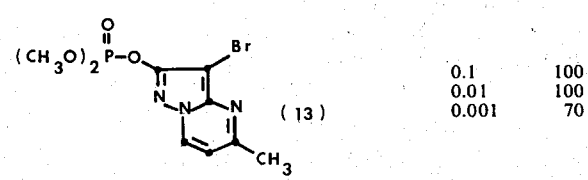 (13) | | 0.1<br>0.01<br>0.001 | 100<br>100<br>70 |

Table 3-continued
(*Myzus* test)
| Active compound | | Active compound concentration in % by weight | Degree of destruction in % after 1 day |
|---|---|---|---|
| 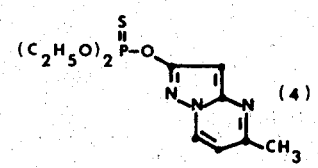 | (4) | 0.1<br>0.01<br>0.001 | 100<br>100<br>98 |
| 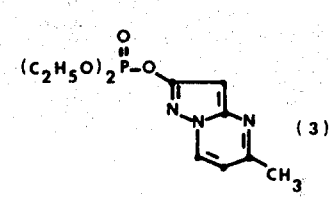 | (3) | 0.1<br>0.01<br>0.001 | 100<br>100<br>95 |
| 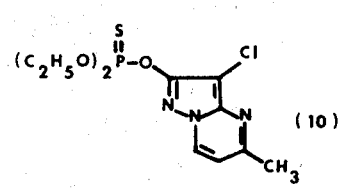 | (10) | 0.1<br>0.01<br>0.001 | 100<br>100<br>70 |
| 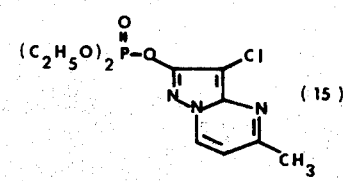 | (15) | 0.1<br>0.01<br>0.001 | 100<br>99<br>80 |
| 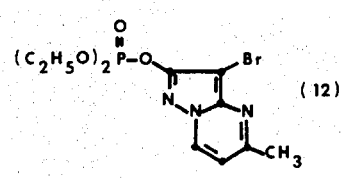 | (12) | 0.1<br>0.01<br>0.001 | 100<br>100<br>75 |
| 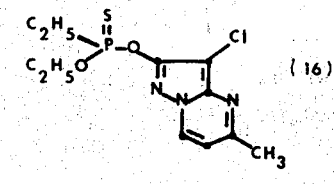 | (16) | 0.1<br>0.01<br>0.001 | 100<br>100<br>100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm., were sprayed with the preparation of the active compound until dripping wet. These bean plants were heavily infested with the two-spotted spider mite (*Tetranychus urticae*) in all stages of development.

Afer the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table 4:

Table 4

| (*Tetranychus* test/resistant) Active compound | Active compound concentration in % by weight | Degree of destruction in % after 2 days |
|---|---|---|
| 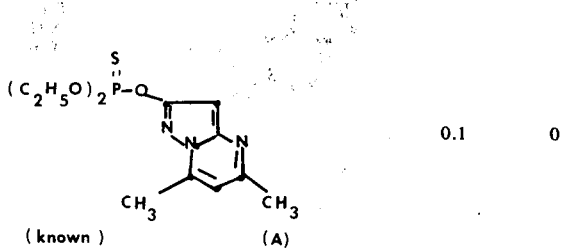 (known) (A) | 0.1 | 0 |
| 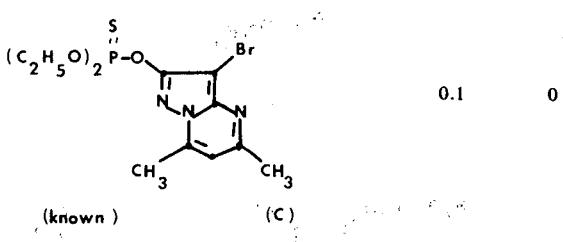 (known) (C) | 0.1 | 0 |
| 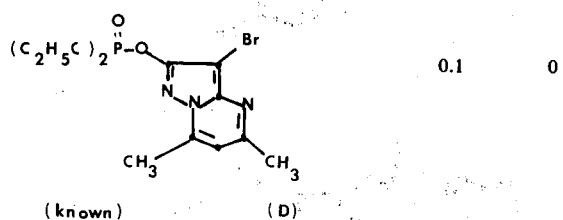 (known) (D) | 0.1 | 0 |
| 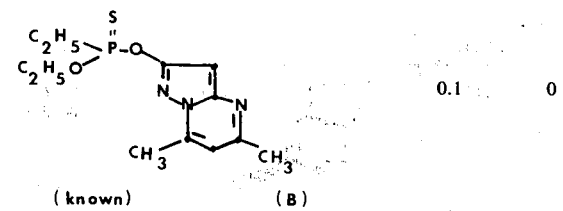 (known) (B) | 0.1 | 0 |

Table 4-continued

| (*Tetranychus* test/resistant) Active compound | Active compound concentration in % by weight | Degree of destruction in % after 2 days |
|---|---|---|
| 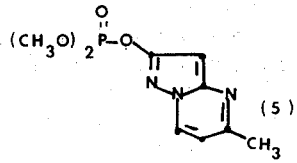 (5) | 0.1<br>0.01 | 100<br>40 |
| 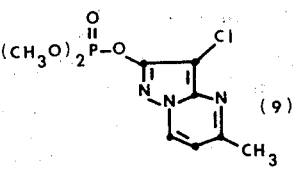 (9) | 0.1 | 100 |
| 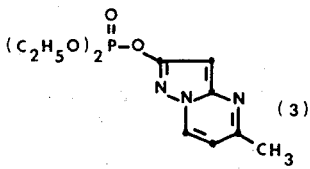 (3) | 0.1<br>0.01 | 100<br>40 |
| 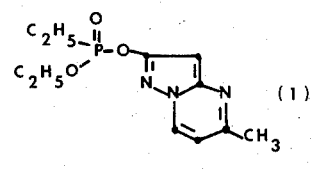 (1) | 0.1 | 99 |

EXAMPLE 5

The 2-hydroxypyrazolopyrimidine derivatives (III) required as starting materials can be prepared, for example, as described below:

a) 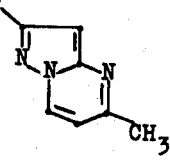

1 mole of methanol-free sodium methylate was suspended in 400 ml of dry ether and 74 g of ethyl formate and 58 g of acetone were added, in the course of which the internal temperature of the mixture rose to 25°–27°C. The batch was stirred overnight and was then evaporated on a water bath, in the course of which the bath temperature did not rise above 70°C, the reaction mixture was cooled and the residue was dissolved in 400 ml of water. This solution was added to a mixture of 99 g of aminopyrazolone, 300 ml of water and 65 g of glacial acetic acid. The batch was stirred for a further 3 hours, the precipitate was filtered off and washed with acetonitrile and the product was dried on clay. 45 g (30% of theory) of 2-hydroxy-5-methylpyrazolo(1,5-α)-pyrimidine of melting point 204°C were obtained.

b)

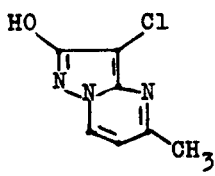

45 g (0.3 mole) of the 2-hydroxy-5-methyl-pyrazolopyrimidine obtained as under (a) were dissolved in 400 ml of glacial acetic acid and 21.3 g of chlorine were passed into this solution at 70°C. After stirring for one hour, the reaction solution was cooled, 24 g of sodium hydroxide in 50 ml of water were added, the mixture was subsequently heated to 40°C for 2 hours and again cooled, and the precipitate was filtered off, washed with water and ether and dried on clay. 18 g (33% of theory) of 2-hydroxy-3-chloro-5-methyl-pyrazolo-(1,5-α)-pyrimidine of melting point 271°C were obtained.

c)

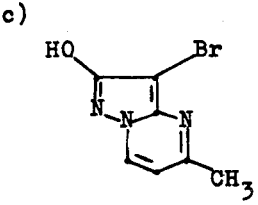

48 g of bromine dissolved in 400 ml of glacial acetic acid were added dropwise, at 70°C, to 45 g (0.3 mole) of the 2-hydroxy-5-methylpyrazolopyrimidine obtained as under a), in 400 ml of glacial acetic acid. After stirring for one hour, the reaction solution was cooled and 24 g of sodium hydroxide in 50 ml of water were added. Thereafter the mixture was briefly heated to 90°C, stirred for a further hour and cooled to approximately 20°C and the precipitate was filtered off, washed with ethanol and ether and dried. 50 g (73% of theory) of 2-hydroxy-3-bromo-5-methyl-pyrazole-(1,5-α)-pyrimidine of decomposition point 185°C were obtained.

EXAMPLE 6:

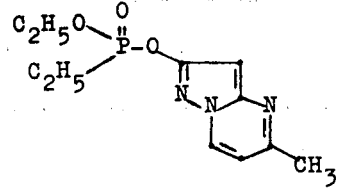
(1)

16 g (0.1 mole) of O-ethyl-ethane-phosphonic acid ester chloride were added to a mixture of 15 g (0.1 mole) of 2-hydroxy-5-methyl-pyrazolo(1,5-α)-pyrimidine and 15 g of potassium carbonate in 100 ml of acetonitrile, in the course of which the temperature of the reaction mixture rose to 25°–40°C. The mixture was stirred overnight aand subsequently filtered, the solvent was distilled off and the crystalline residue was recrystallized from a ligroin/ethyl acetate mixture, 19 g (71% of theory) of O-ethyl-ethane-O-[5-methyl-pyrazolo(1,5-α)-pyrimidin-(2)-yl]-phosphonic acid ester of melting point 76°C were obtained.

EXAMPLE 7

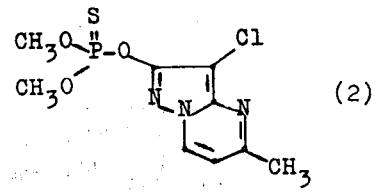
(2)

16 g (0.1 mole) of O,O-dimethyl-thionophosphoric acid ester chloride were added to 18.5 g (0.1 mole) of 2-hydroxy-3-chloro-5-methylpyrazolo-(1,5-α)-pyrimidine and 15 g of potassium carbonate in 100 ml of acetonitrile and the mixture was stirred for 2 hours at 40°C and subsequently stirring was continued at room temperature overnight. The reaction mixture was then poured into water and extracted by shaking with methylene chloride, the organic phase was dried over sodium sulfate, the solvent was distilled off and the residue was recrystallized from ligroin/ethyl acetate. 10.5 g (33% of theory) of O,O-diethyl-O-[3-chloro-5-methyl-pyrazolo-(1,5-α)-pyrimidin(2)yl]-thionophosphoric acid ester of melting point 114°C were obtaind.

The following compounds were prepared analogously to those of Examples 6 and 7.

| Structure | Physical properties (melting point) |
|---|---|
| 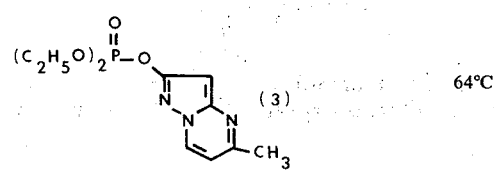 (3) | 64°C |

-continued
| Structure | Physical properties (melting point) |
|---|---|
| 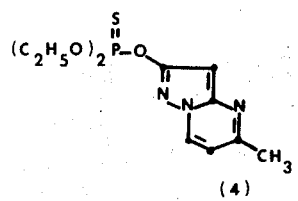 (4) | 90°C |
| 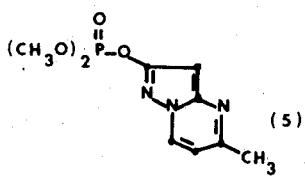 (5) | 110°C |
| 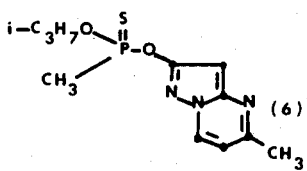 (6) | 92°C |
| 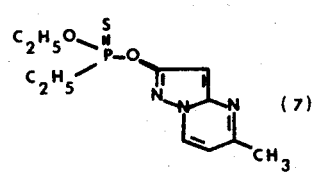 (7) | 94°C |
| 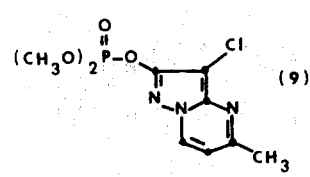 (9) | 80–81°C |
| 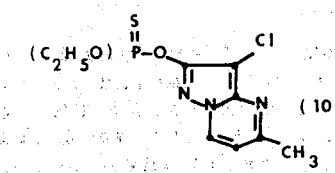 (10) | 88°C |

-continued

| Structure | | Physical properties (melting point) |
|---|---|---|
| (C₂H₅O)₂P(=S)-O-[4-bromo-6-methylpyrazolo-pyrimidine] | (11) | 106°C |
| (C₂H₅O)₂P(=O)-O-[4-bromo-6-methylpyrazolo-pyrimidine] | (12) | 48°C |
| (CH₃O)₂P(=O)-O-[4-bromo-6-methylpyrazolo-pyrimidine] | (13) | 86–87°C |
| C₂H₅O(C₆H₅)P(=S)-O-[4-bromo-6-methylpyrazolo-pyrimidine] | (14) | 81–83°C |

Other compounds which can be similarly prepared include:

O,O-di-pentyl-O-[5-methylpyrazolo(1,5-α)-pyrimidin-(2)-yl]-thionophosphoric acid ester, O-hexyl-butane-O-[5-methylpyrazolo(1,5-α)-pyrimidin-(2)-yl]-thionophosphonic acid ester, and the like.

It will be appreciated that the instant specification and examples are set forth by way of illustration and not limitation, and that various modifications and changes may be made without departing from the spirit and scope of the present invention.

What is claimed is:

1. An O-pyrazolopyrimidine-(thiono)-phosphoric(-phosphonic) acid ester of the formula

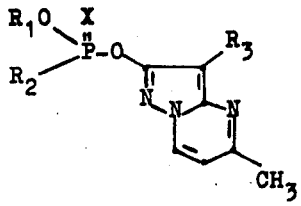

(I)

in which
  $R_1$ is alkyl of 1 to 6 carbon atoms,
  $R_2$ is alkyl of 1 to 4 carbon atoms, alkoxy of 1 to 6 carbon atoms or phenyl,
  $R_3$ is hydrogen, chlorine or bromine, and
  X is oxygen or sulfur.

2. A compound according to claim 1 in which $R_1$ is alkyl of 1 to 4 carbon atoms and $R_2$ is alkyl of 1 to 3 carbon atoms, alkoxy of 1 to 4 carbon atoms or phenyl.

3. The compound according to claim 1 wherein such compound is O,O-dimethyl-O-[5-methylpyrazolo(1,5-α)-pyrimdin-(2)-yl]-thionophosphoric acid ester of the formula

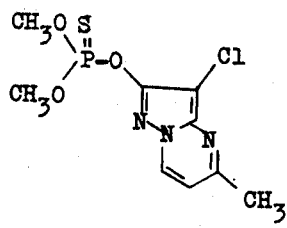

(2)

4. The compound according to claim 1 wherein such compound is O,O-dimethyl-O-[5-methylpyrazolo(1,5-α)-pyrimidin-(2)-yl]-phosphoric acid ester of the formula

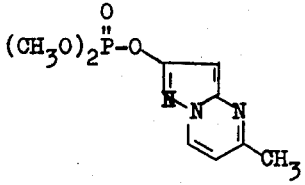

(5)

5. The compound according to claim 1 wherein such compound is O,O-diethyl-O-[3-chloro-5-methyl-pyrazolo(1,5-α)-pyrimidin-(2)-yl]-thionophosphoric acid ester of the formula

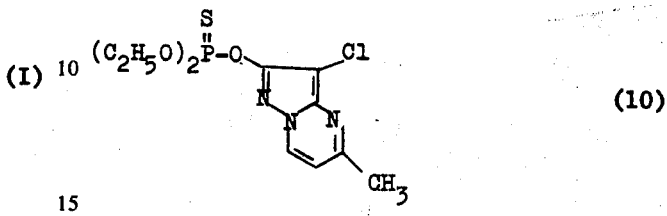

(10)

6. The compound according to claim 1 wherein such compound is O,O-diethyl-O-[3-bromo-5-methyl-pyrazolo(1,5-α)-pyrimidin-(2)-yl]-thionophosphoric acid ester of the formula

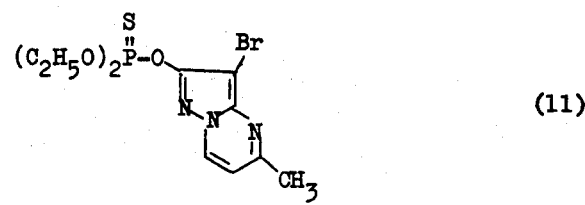

(11)

7. The compound according to claim 1 wherein such compound is O-ethylethane-O-[3-chloro-5-methyl-pyrazolo(1,5-α)-pyrimidin-(2)-yl]-thionophosphonic acid ester of the formula

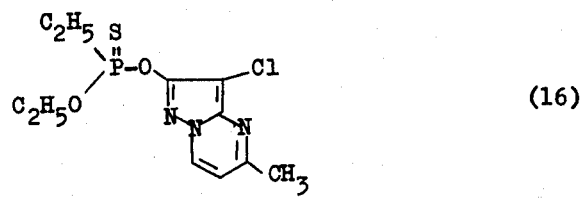

(16)

* * * * *